United States Patent
Parasher et al.

(10) Patent No.: US 7,048,684 B2
(45) Date of Patent: May 23, 2006

(54) PROBE VIBRATING ASSEMBLY FOR ENDOSCOPIC PROCEDURES

(76) Inventors: Vinod K. Parasher, 102 Corn Tassle St., Rehobeth Beach, DE (US) 19971; Norman J. Miller, 17 Black Duck Way, Georgetown, DE (US) 19947

( * ) Notice: Subject to any disclaimer, the term of this patent is extended or adjusted under 35 U.S.C. 154(b) by 0 days.

(21) Appl. No.: 10/803,511

(22) Filed: Mar. 18, 2004

(65) Prior Publication Data

US 2004/0199049 A1    Oct. 7, 2004

Related U.S. Application Data

(60) Provisional application No. 60/456,329, filed on Mar. 20, 2003.

(51) Int. Cl.
*A61B 1/00* (2006.01)

(52) U.S. Cl. ............... 600/104; 600/102; 600/126; 600/156; 606/169

(58) Field of Classification Search ............... 600/104, 600/106, 124; 606/169
See application file for complete search history.

(56) References Cited

U.S. PATENT DOCUMENTS

| | | | |
|---|---|---|---|
| 3,642,002 A * | 2/1972 | Otterstrom | 606/177 |
| 4,735,604 A * | 4/1988 | Watmough et al. | 604/22 |
| 5,312,418 A * | 5/1994 | Bonnet | 606/128 |
| 6,764,439 B1 * | 7/2004 | Schaaf et al. | 600/106 |
| 6,817,973 B1 * | 11/2004 | Merril et al. | 600/118 |

OTHER PUBLICATIONS

Boston Scientific Corp.—Rotablator 2003.

* cited by examiner

*Primary Examiner*—Beverly M. Flanagan
*Assistant Examiner*—Matthew J. Kasztejna

(57) ABSTRACT

A probe vibrating assembly for endoscopic procedures includes a base unit having a rotatable spindle. A drive member is eccentrically mounted to the spindle. The drive unit is secured to a slide plate to move the slide plate back and forth while the spindle is rotating. A clamp mechanism is secured to the slide plate and is used for clamping a probe so that the probe also moves back and forth. The probe is mounted to a medical scope.

20 Claims, 3 Drawing Sheets

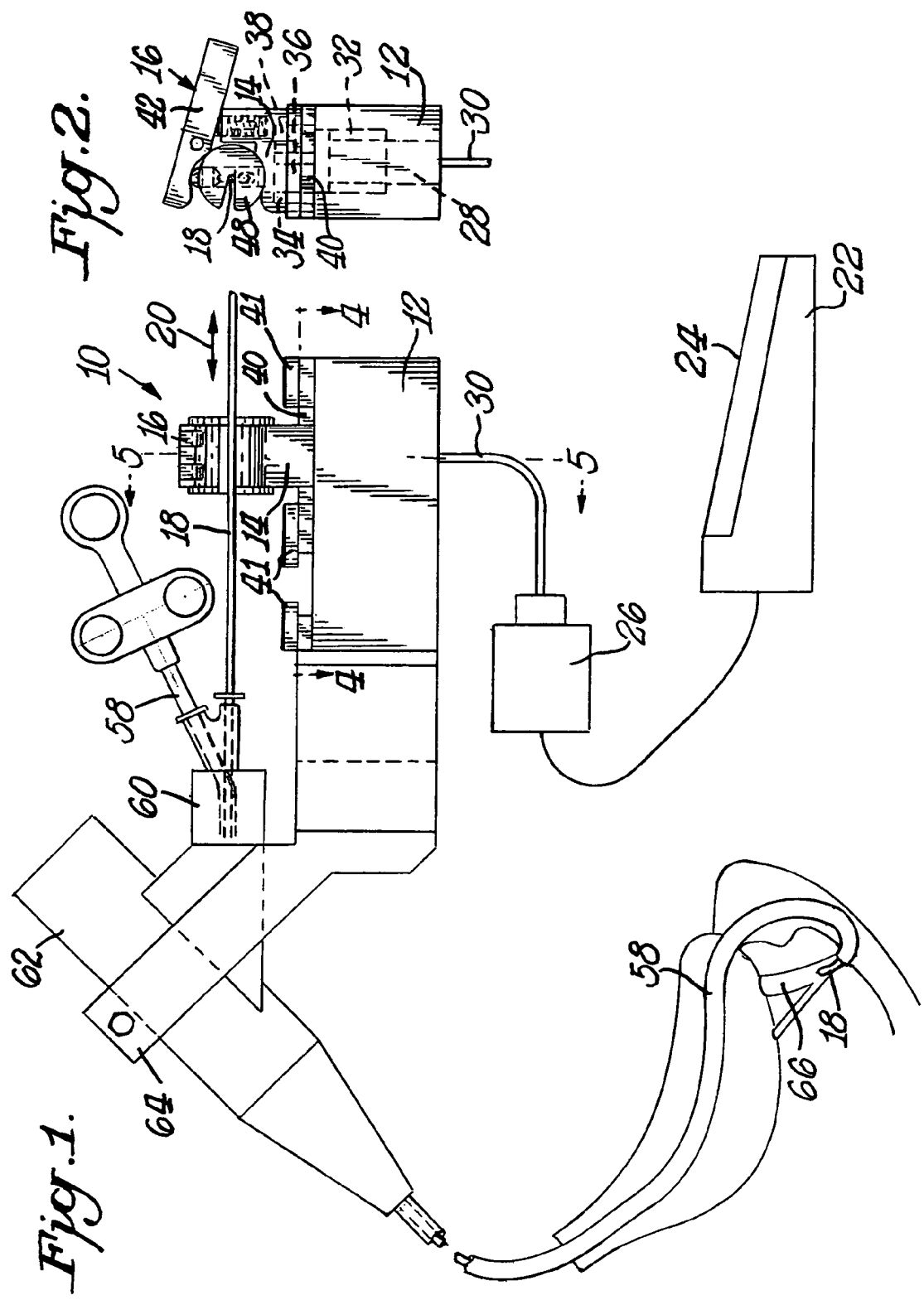

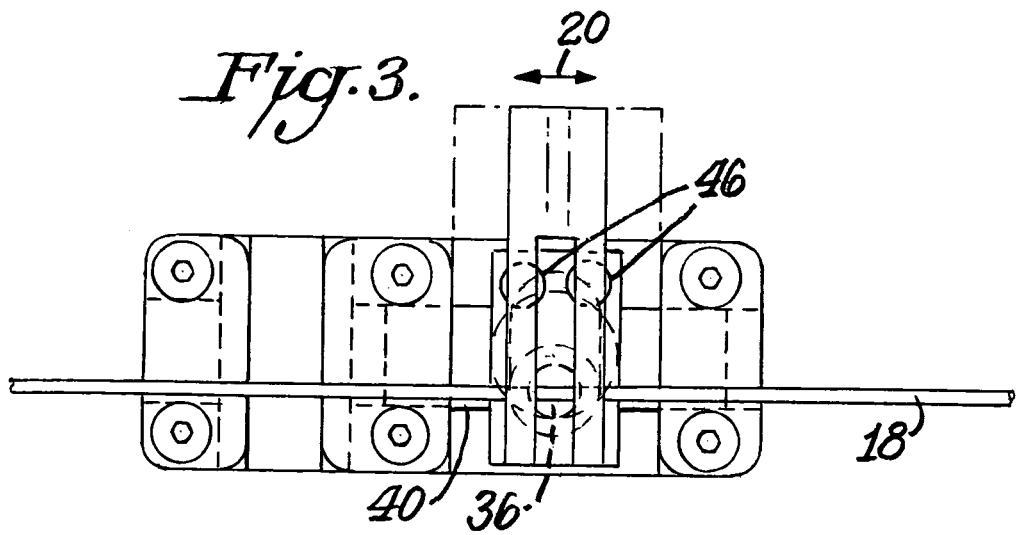
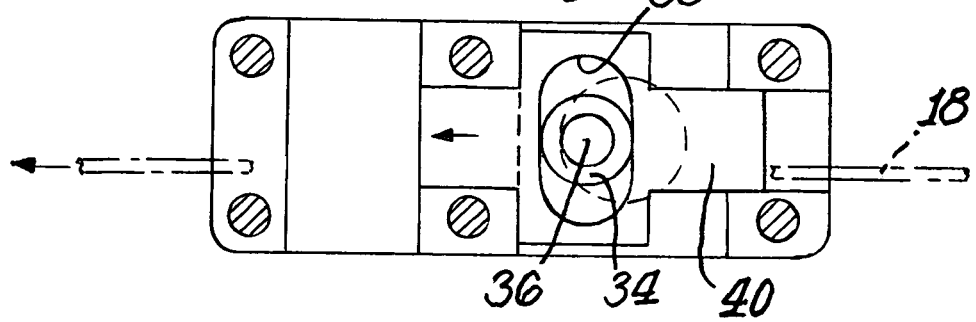
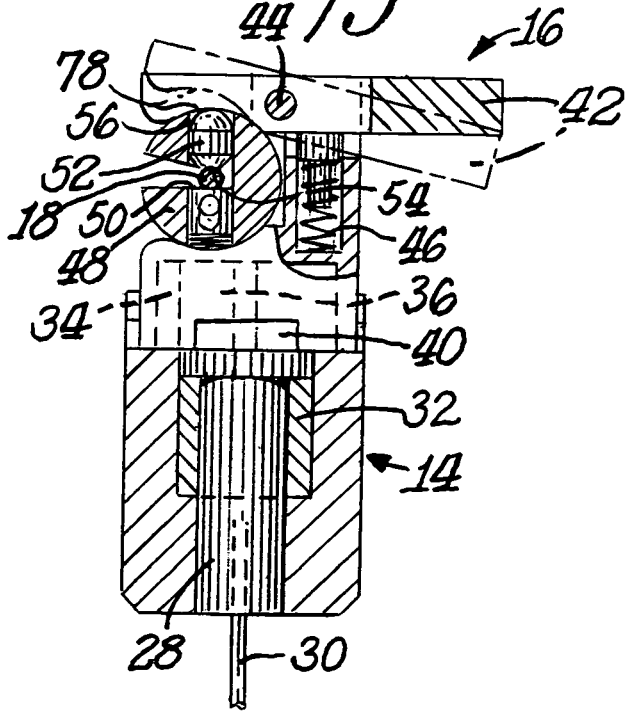

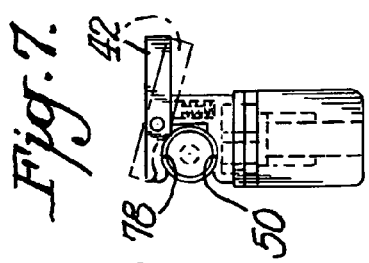
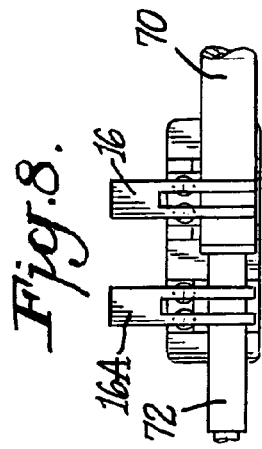
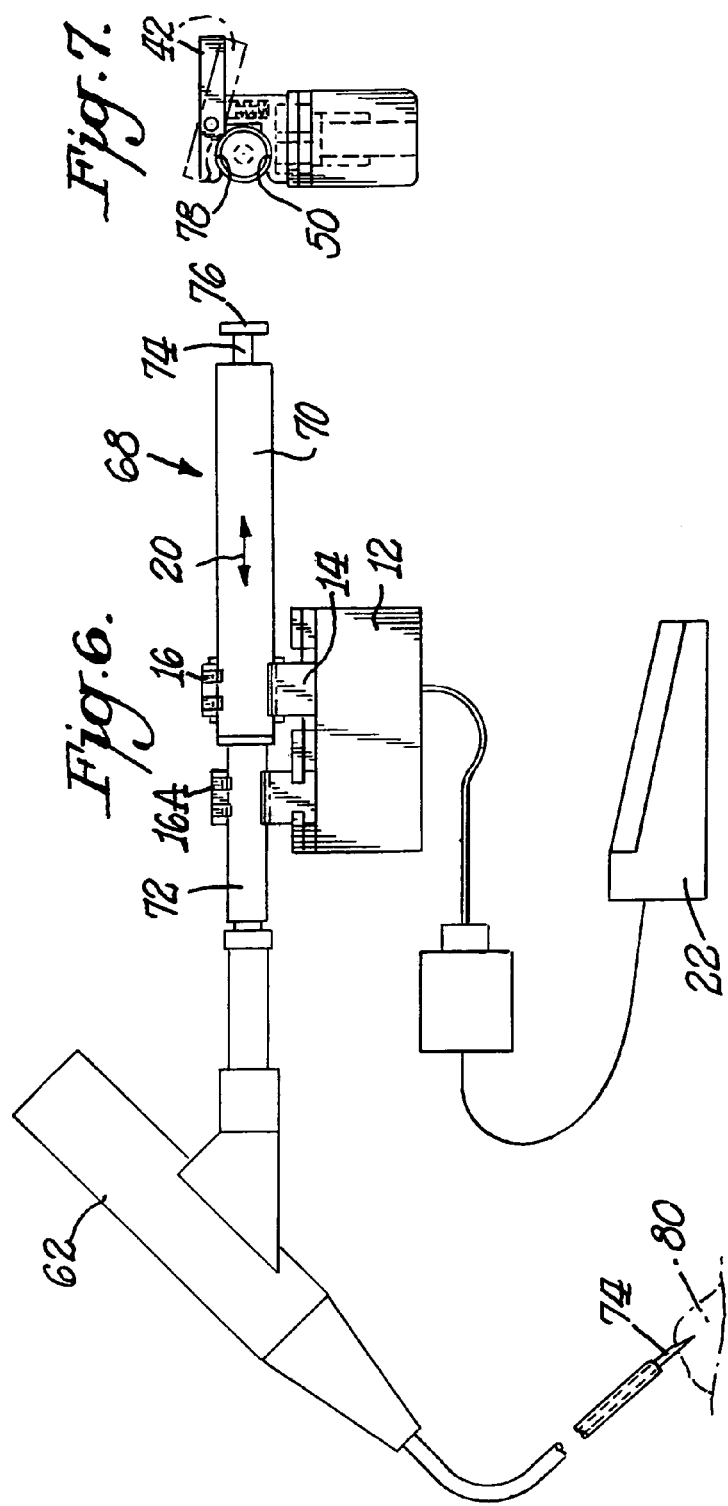

PROBE VIBRATING ASSEMBLY FOR ENDOSCOPIC PROCEDURES

CROSS-REFERENCE TO RELATED APPLICATION

This application is based upon provisional application Ser. No. 60/456,329, filed Mar. 20, 2003.

BACKGROUND OF THE INVENTION

Various endoscopic procedures are used which involve the insertion of probe type devices such as a wire or needle into difficult to reach portions of the body for various medical purposes. For example, Endoscopic Retrograde Chlongio Pancreato Graphy (ERCP) utilizes a wire inserted into the bile duct. Since the bile duct is a difficult to reach area, there are difficulties with the conventional prior art techniques in locating the bile duct entrance. For example, it is necessary for the wire to enter the bile duct opening (pappila of vater) which might be only a 5 millimeter opening in order to locate the endoscope viewing area in the bile duct and pancreatic duct. This is conventionally done under fluoroscopy and conventionally is a blind process where a thin wire inserted through a catheter blindly probes by twirling or rotating the wire until the opening is found. It would be desirable if some technique could be developed wherein the surgeon can have a more convenient and more accurate procedure for inserting the wire into the bile duct opening.

Another known technique which utilizes an endoscope at difficult to reach areas involves the retrieval of cancerous cells by use of a fine needle to break up the cells in the tumor and then obtain the specimen from the cells through aspiration.

SUMMARY OF THE INVENTION

An object of this invention is to provide improvements in the ERCP procedure which avoids the problems of the prior art.

A further object of this invention is to provide improvements in the biopsy techniques for obtaining cancer cells and particularly to increase the yield of cancer cells.

In accordance with this invention a probe vibrating assembly is provided wherein a wire or needle is clamped to an oscillating mechanism in order to vibrate the wire or needle so that the wire or needle moves to and fro to better locate the difficult to reach areas. Where a wire is used the wire could function as a guide wire to facilitate the insertion of the catheter and the endoscope viewing area into the difficult to reach location. Where a fine needle is used, the vibration of the needle could effectively break up the cancer cells and thereby facilitate the aspiration or suction of the cells so as to increase the yield of the cancer cells that could be used for test purposes.

BRIEF DESCRIPTION OF THE DRAWINGS

FIG. 1 is a side elevational view of a wire probe vibrating assembly for endoscopic procedures;

FIG. 2 is a right end elevational view of the assembly shown in FIG. 1 with the clamp in an open position;

FIG. 3 is an enlarged top plan view of a portion of the assembly shown in FIGS. 1–2;

FIG. 4 is an enlarged cross-sectional view taken through line 4—4 of FIG. 1;

FIG. 5 is an enlarged right elevational view taken through the line 5—5 of FIG. 1;

FIG. 6 is a side elevational view of a modified form of vibrating system in accordance with a further aspect of this invention where the probe is a needle;

FIG. 7 is a right side elevational view of the assembly shown in FIG. 6; and

FIG. 8 is a top plan view of a portion of the assembly shown in FIGS. 6–7.

DETAILED DESCRIPTION

The present invention, in general, involves a system which includes an elongated flexible probe attached to an endoscope. The probe is clamped to a vibration creating assembly which may be actuated in any manner such as by a foot pedal to vibrate the probe in a to and fro motion. The use of a foot pedal permits the surgeon to control the vibration and probe movements which could range from speeds of 15 rpm to 8,000 rpm or more, preferably 100 rpm to 3,000 rpm or 4,000 rpm.

The probe may be a wire which would act as a guide wire for finding an opening such as the bile duct opening to facilitate the movement of a catheter through that opening and into a difficult to reach location, such as a bile duct, for viewing by the endoscope. Alternatively, the probe could be a fine needle whereby the vibrating needle would break up cancer cells of a tumor to increase the yield of cells retrieved through aspiration or other conventional techniques.

Where the probe is a guide wire the wire would be of floppy or flexible structure so that the longitudinal vibration of the wire readily finds its way into the opening which then permits more conventional procedures such as used in ERCP to be used. Such guide wire could be removed or left in place. While specific reference is made to the bile duct the same practices could be used for other difficult to locate regions such as the pancreatic duct.

Once the probe has served its function of entering the difficult to locate areas the conventional techniques, such as endoscopic ultrasound could be used.

The invention could be used to identify mass tumors in a manner more effective than MRI.

Where the probe is a fine needle the needle would pass through areas such as the pancreas and would be used to break cancer cells which would then be removed through suction or aspiration such as by a suction syringe where the materials are squirted onto a slide. Sufficient passes could be used to obtain the desired amount of test tissue. The needle could be the vibrating pointed tip of the probe which would be inserted into a tumor to break the cells as a result of the longitudinal vibration of the needle thereby facilitating suction retrieval. If desired, the needle may have an axial stylet to facilitate unblocking the needle as the needle vibrates.

In general, the system includes structure for creating a rotary motion that is converted into an oscillating linear motion to oscillate the probe back and forth over a predetermined length. Preferably, the probe is driven by a high variable speed mechanism which is preferably controlled with a foot pedal. It is to be understood, however, that other actuating and speed control structures could be used within the practice of the invention. The probe is preferably clamped with a spring clamp to permit quick load and release. This subassembly is desired to slide so that as the probe is being vibrated the probe can be extended or retracted within a catheter as desired without effecting the frequency of the vibration. These features create great potential for a successful process. This subassembly is then preferably attached to an endoscope so that the vibration could be maximized eliminating the loss of vibration between the scope and the vibrator.

FIGS. 1–5 illustrate a probe vibrating assembly 10 in accordance with this invention. As shown therein assembly 10 includes a main body 12. An oscillating head 14 is mounted on main body 12. Oscillating head includes a clamp mechanism 16 which is used for clamping a probe in the form of a wire 18 for oscillating movement as shown by the arrow 20.

The actuation and control of the speed of oscillation may be accomplished in any suitable manner. FIG. 1 shows a variable speed foot pedal 22 having a pivoted actuating surface 24. A surgeon, for example, would control the speed by the extent of depression of surface 24 when the surgeon's foot is placed on surface 24. Variable speed foot pedal 22 is electrically connected to a variable speed motor 26 which in turn rotates a spindle 28 through its connection from flexible cable 30. See FIGS. 2 and 5. Spindle 28 rotates about its central axis within roller bearings 32. Positioned in roller bearings 34 is a drive member 36 eccentrically mounted to spindle 28 and connected as part of oscillating head 14.

Instead of controlling the speed through a variable speed foot pedal, a manually operable variable speed control mechanism could be used. Such manually operable variable speed control could include an on/off switch and a manually rotatable dial on the control housing could be rotated to select the desired speed. The manual speed control mechanism could be electrically connected to variable speed motor 26 which would then operate in the same manner as when activated by the variable speed foot pedal 22.

When spindle 28 is rotated under the actuation of motor 26 and variable speed control, such as foot pedal 22, spindle 28 rotates about its longitudinal axis. During this rotation the eccentric mounting of drive member 36 causes the drive member 36 to move in an eccentric path with its longitudinal axis spaced from the longitudinal axis of spindle 28.

As shown in FIG. 4 drive member 36 is mounted in an elongated slot 38 in slide plate 40 causing slide plate 40 to reciprocate back and forth in a path perpendicular to the axis of spindle 28 as indicated by the arrow 20 of FIG. 1.

The clamp mechanism 16 is mounted to oscillating head 14. As best shown in FIG. 5 and also shown in FIG. 2 clamp mechanism 16 includes a pivotally mounted U-shaped lever 42 mounted about pivot pin 44. Lever 42 is spring biased by means of two sets of springs 46 in a closing or counterclockwise direction. Lever 42 is disposed against a generally cylindrical clamp housing 48. Mounted within clamp housing 48 is a fixed clamp seat 50 and a movable clamping member 52. Housing 48 also includes a notch 54 of a shape to receive wire 18. When it is desired to clamp the wire 18 in the clamp mechanism 16, lever 42 is pushed downwardly in a clockwise direction as shown in phantom in FIG. 5. This permits clamping member 52 to be capable of moving upwardly in passageway 56 of clamp housing 48. Wire 18 is then inserted into clamp housing 48 on seat 50 and against notch 54. Lever 42 is then released and is moved in a counter-clockwise direction under the influence of springs 46 to firmly clamp wire 18 in place. As illustrated the lower portion of clamp member 52 may be shaped to conform to the shape of wire 18 or may include serrations to better grip the wire.

As shown in FIG. 1 wire 18 is inserted into a conventional catheter 58 which is mounted in a passageway in block 60 and extends into a medical scope or endoscope 62. Endoscope 62 is detachably secured by clamp mechanism 64 to main body 12. Clamp mechanism 64 may take any suitable form such as by being a pair of pivotally mounted clamp members each of which has an arcuate groove or indent for receiving the circular endoscope body. Catheter 58 extends through scope 62 with wire 18 extending out of catheter 58. Catheter 58 and wire 18 is inserted into the area near the bile duct 66. Wire 18 is vibrated back and forth until it enters the bile duct opening at which point the endoscope can view the bile duct and normal ERCP procedures can be used.

As shown in FIG. 1 slide plate 40 is guided in its vibrating movement by being mounted under retainer plates 41 to confine the slide plate against the top of body 12 while the slide plate is moving back and forth.

FIGS. 6–8 show an alternative use of assembly 10 for collecting specimens such as cancerous tissue from a tumor. As shown therein the clamping mechanism 16 would be used for mounting the probe assembly 68. As illustrated probe assembly 68 includes an outer cylinder 70 and a plunger 72. A thin flexible needle 74 is inserted through cylinder 70 and plunger 72. Needle 74 could be attached to a pull handle 76.

As illustrated in FIG. 7 the cylinder 70 would be mounted against seat 50 of clamp mechanism 16 by having the arcuate inner surface 78 of lever 42 spring biased to the closing position in the same manner as the clamping of wire 18. A second clamping mechanism 16A would be used for clamping against the plunger 72. Clamp mechanism 16A differs from clamp mechanism 16 in that clamp mechanism 16A is fixed or stationary, thus remaining in one position whereas clamp mechanism 16 would move back and forth as shown by the arrow 20 to thereby move the cylinder 70 and needle 74 back and forth in a vibratory manner. Needle 74 would extend through medical scope 62 and be disposed against tumor 80 so that the vibrating motion would cause a break up the tumor tissue to permit, for example, cancerous tissue to be removed under the suction created when handle 76 is pulled outwardly.

The invention may be broadly practiced where any form of vibration is used to cause a needle, wire or other collecting device to collect cells, such as, but not limited to cancerous tissue.

As is apparent the assembly provides quick change capability for either of the options of using a vibrating wire or a vibrating needle. The fixed head or clamp mechanism 16A can be removed for one option and a wire adapter can be provided to clamp the wire for this same procedure.

Accordingly, the same basic probe vibrating assembly 10 could be used to vibrate a probe in the form of a wire or a probe in the form of a needle.

What is claimed is:

1. A probe vibrating assembly for endoscopic procedures comprising a main body, a spindle in said main body, a drive mechanism for rotating said spindle, a drive member eccentrically mounted to said spindle, a clamp mechanism, said eccentrically mounted drive member being secured to said clamp mechanism for moving said clamp mechanism back and forth in accordance with the movement of said eccentric drive member, a cylinder clamped in said clamp mechanism, said clamp mechanism thereby causing said cylinder to move back and forth in response to the movement of said clamp mechanism, a probe extending through said cylinder with said cylinder being transversely between said clamp mechanism and said probe, and said probe being mounted for joint back and forth movement with said cylinder in response to the back and forth movement of said cylinder, a medical scope, said probe mounted to said medical scope, and said probe extending outwardly beyond said medical scope.

2. The assembly of claim 1 including a catheter mounted to said medical scope and extending through said medical scope, and said probe being a guide wire disposed in said catheter.

3. The assembly of claim 1 wherein said probe is a flexible needle terminating in a knife edge for breaking up a tumor tissue to facilitate the tissue being removed, and said medical scope being a flexible endoscope.

4. The assembly of claim 3 including a plunger telescopically mounted in said cylinder for relative motion between said cylinder and said plunger, and said needle extending through said cylinder and said plunger.

5. The assembly of claim 4 wherein said plunger and cylinder comprise part of an aspiration structure for retrieving tissue contacted by said needle.

6. The assembly of claim 5 wherein said aspiration structure further includes a pull handle mounted to the outer end of said needle outwardly of said cylinder whereby the outward pulling of said pull handle creates a suction to permit broken up tissue to be removed.

7. The assembly of claim 3 wherein said spindle is driven by a variable speed control.

8. The assembly of claim 3 wherein said spindle is rotatable about its longitudinal axis, said drive member being part of an oscillating head, said eccentrically mounted drive member moving in an eccentric path with the longitudinal axis of said drive member being spaced from said longitudinal axis of said spindle, and said drive member being mounted in an elongated slot in a slide plate in said oscillating head to move said slide plate in a back and forth direction perpendicular to said longitudinal axis of said spindle.

9. The assembly of claim 3 wherein said clamp mechanism includes a clamp housing, said clamp housing having a seat for receiving said cylinder, a pivotally mounted lever located at said clamp housing, and said pivotally mounted lever having a clamping end biased in a direction toward said seat of said clamp housing whereby said cylinder may be clamped between said seat and said clamping end.

10. The assembly of claim 3 wherein said medical scope is detachably mounted to said main body.

11. The assembly of claim 1 wherein said back and forth movement is in a direction perpendicular to the longitudinal axis of said spindle.

12. The assembly of claim 3 wherein a pull handle is mounted to the outer end of said needle outwardly of said cylinder.

13. The assembly of claim 12 wherein said clamp mechanism includes a clamp housing, said clamp housing having a seat for receiving said cylinder, a pivotally mounted lever located at said clamp housing and said pivotally mounted lever having a clamping end biased in a direction toward said seat of said clamp housing whereby said cylinder may be clamped between said seat and said clamping end, said clamping end of said lever having an arcuate recess, and said seat having an arcuate recess for receiving said cylinder.

14. A probe vibrating assembly for endoscopic procedures comprising a main body, a spindle in said main body, a drive mechanism for rotating said spindle, a drive member eccentrically mounted to said spindle, a clamp mechanism, said eccentrically mounted drive member being secured to said clamp mechanism for moving said clamp mechanism back and forth in accordance with the movement of said eccentric drive member, a cylinder clamped in said clamp mechanism, said clamp mechanism thereby causing said cylinder to move back and forth in response to the movement of said clamp mechanism, a probe extending through said cylinder and mounted for joint back and forth movement with said cylinder, a medical scope, said probe mounted to said medical scope, said probe extending outwardly beyond said medical scope, a plunger telescopically mounted in said cylinder for relative motion between said cylinder and said plunger, said needle extending through said cylinder and said plunger, a clamping assembly spaced from said clamp mechanism, said plunger being clamped in said clamp assembly, said clamp assembly being fixedly mounted against longitudinal movement to maintain said plunger in a fixed position, and said clamp mechanism being mounted for reciprocal longitudinal movement to move said cylinder back and forth.

15. The assembly of claim 1 wherein said spindle is rotatable about its longitudinal axis, said drive member being part of an oscillating head, said eccentrically mounted drive member moving in an eccentric path with the longitudinal axis of said drive member being spaced from said longitudinal axis of said spindle, and said drive member being mounted in an elongated slot in a slide plate in said oscillating head to move said slide plate in a back and forth direction perpendicular to said longitudinal axis of said spindle.

16. A probe vibrating assembly for endoscopic procedures comprising a main body, a spindle in said main body, a drive mechanism for rotating said spindle, a drive member eccentrically mounted to said spindle, a clamp mechanism, said eccentrically mounted drive member being secured to said clamp mechanism for moving said clamp mechanism back and forth in accordance with the movement of said eccentric drive member, a cylinder clamped in said clamp mechanism, said clamp mechanism thereby causing said cylinder to move back and forth in response to the movement of said clamp mechanism, a probe extending through said cylinder and mounted for joint back and forth movement with said cylinder, a medical scope, said clamp mechanism including a clamp housing, said clamp housing having a seat for receiving said cylinder, a pivotally mounted lever located at said clamp housing, and said pivotally mounted lever having a clamping end biased in a direction toward said seat of said clamp housing whereby said cylinder may be clamped between said seat and said clamping end.

17. The assembly of claim 16 wherein a movable clamping member is located in a passageway in said clamp housing in line with said seat, a notch located in said clamp housing adjacent said seat, said notch having an arcuate shape corresponding to the shape of said cylinder, said movable clamping member being in the path of movement of said clamping end of said lever whereby said clamping end of said lever pushes said movable clamping member into clamping engagement with said cylinder, and whereby said lever may be moved in an opposite direction from its closing direction to release said movable clamping member from clamping arrangement with said cylinder.

18. In an endoscopic method comprising providing a flexible probe mounted to a rotatable spindle, disposing the probe through a flexible medical scope with the probe extending longitudinally outwardly of the medical scope, inserting the probe and the medical scope into a patient, rotating the spindle, converting the rotation of the spindle into a back and forth longitudinal reciprocal movement of the probe without rotation of the probe, and using the longitudinal reciprocal movement of the probe to guide the medical scope in its passage into a patient until the medical scope reaches a hard to reach location of the patient which requires the medical scope for the viewing that location of the patient.

19. The method of claim 18 wherein the hard to reach location is selected from the group consisting of the bile duct and the pancreatic duct.

20. The method of claim 18 wherein the method is selected from the group consisting of ERCP, and the breaking and removal of cancer cells.

* * * * *